US006489166B1

(12) United States Patent
Kang et al.

(10) Patent No.: US 6,489,166 B1
(45) Date of Patent: Dec. 3, 2002

(54) PLANT REGENERATION METHOD FOR MATURE SEED-DERIVED CALLUS IN ZOYSIAGRASS

(75) Inventors: Jeong-Gu Kang, Kwangju (KR); Pill-Soon Song, Kwangju (KR); Chung-Mo Park, Kwangju (KR); Tohyama Kohichi, Chunlanam-Do (KR); Hyo Yeon Lee, Chunlanam-Do (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 09/915,294

(22) Filed: Jul. 27, 2001

(51) Int. Cl.$^7$ ................................................ C12N 5/00
(52) U.S. Cl. .................................................... 435/430.1
(58) Field of Search ....................................... 435/430.1

(56) References Cited

PUBLICATIONS

Hiei et al, The Plant Journal, vol. 6(2), Efficient transformation of rice (Oryza sativa L.) . . . , pp. 271–282, 1994.
Inokuma et al, Plant Cell Reports, vol. 15, "Plant regeneration from protoplasts of Japanese . . . ", pp. 737–741, 1996.
Ke et al, Plant Cell Reports, vol. 15, "Plant regeneration in Kentucky bluegass (Poa pratensis L.) . . . ", pp. 882–887, 1996.
Carvalho et al, Plant Cell Reports, vol. 17, "Type II callus production and plant regeneration . . . ", pp. 76–76, 1997.
Asano et al, Plant Cell, Tissue and Organ Culture, vol. 39, "Improved regeneration response . . . ", pp. 101–103, 1994.
Akasaka et al, Plant Science 156, "Improved plant regeneration From cultured leaf segments in . . . ", pp. 169–175, 2000.
Cho et al, Plant Science 138, "Transformation of recalcitrant Barley cultivars through . . . ", pp. 229–244, 1998.
Ohira et al., Plant & Cell Physiol., vol. 14, "Studies on the nutrition of rice cell cutlure . . . ", pp. 1113–1121, 1973.
Sato et al, Plant Science 113, "Culturing conditions affecting the production of anthocyanin . . . ", pp. 91–98, 1996.

*Primary Examiner*—Bruce R. Campell
*Assistant Examiner*—Annette Para
(74) *Attorney, Agent, or Firm*—Jacobson Holman PLLC

(57) ABSTRACT

Fully differentiated higher plants may be regenerated from undifferentiated plant tissues, such as callus, derived from mature seeds, immature embryos, stems, roots, or leaves. The present invention provides a plant regeneration method from mature seed-derived calli. The regeneration procedure may include the induction of calli on the MS media containing 2 mg/L 2,4-dichlorophenoxyacetic acid and 0.2 mg/L 6-benzylaminopurine, 4 mg/L thiamine-HCl, and 100 mg/L α-ketoglutaric acid. The plant regeneration efficiency is the highest when calli are grown on the MS media supplemented with 3% maltose and 1 mg/L 6-benzylaminopurine or 1 mg/L thidiazuron (TDZ). The invention can be utilized to introduce a gene or genes of agronomically important values into the zoysiagrass or possibly closely related turfgrass species.

5 Claims, 2 Drawing Sheets

PLANT REGENERATION METHOD FOR MATURE SEED-DERIVED CALLUS IN ZOYSIAGRASS

BACKGROUND OF THE INVENTION

The present invention relates to an efficient, reliable plant regeneration method using mature seed-derived callus in zoysiagrass (*Zoysia japonica* Steud.), to the optimised conditions for callus induction and growth from mature seeds, and to the morphological criteria for the selection of callus types that are readily regenerated to mature plants. The invention is critical for plant tissue culture and genetic transformation in this monocot species. Prior to plant regeneration, the cultured callus cells may be genetically transformed with gene expression cassettes.

Turfgrass is widely used for decorative and ground-protective purposes, including golf courses, athletic fields, home gardens, and recreation parks, to improve spatial enjoyment, to decrease dust from ground, and to keep the air clean. As a result, turfgrass is rapidly emerging as a potential commercial target for plant biotechnological applications in recent years. It forms a second largest market size among crop plants in USA, and its application is rapidly growing worldwide. In addition, recent successful achievements of genetic transformation of some turfgrass species have prompted intensive biotechnological researches.

Useful target traits for the genetic manipulation of turfgrass include those to improve ground-covering capacity, tolerance to traffic injury, and regrowth after damage. Resistance to pathogenic infections and adaptability to cold and drought stress are additional targets to be engineered. Among these target traits, the most attractive one is to decrease the cost for regular maintenance, such as watering, mowing, and pathogen control. In USA, more than thirty billion dollars are annually spent just for the regular maintenance. One easy way to achieve these goals is to introduce foreign genes whose physiological activities have been proven in model plants into turfgrass. This method has several advantages over the classical breeding methods. The new trait(s), as a result of such genetic manipulations, can be predicted from the functional analysis in model plants, in which molecular and morphological analysis techniques for the genetic manipulation and tissue culture are well established. It is also possible to introduce more than one gene by a single round of genetic manipulation into any plant species in a predictable way.

However, a technical barrier to be overcome with the turfgrass genetic transformation is that this plant species is extremely reluctant to genetic manipulation, and the tissue culture conditions have not been precisely defined yet, like most of the monocot species. Although a few turfgrass species have been successfully transformed in recent years, the results are not routinely reproducible, and its application to other turfgrass species is very limited so far. This entails that molecular and physiological techniques and systems should be further defined for routine application of the genetic transformation technique to variable turfgrass species. The critical parameters to be refined include the conditions optimized for callus induction and growth and the optimal media compositions, such as nutrients, growth hormones, salt composition, and ionic strength, for plant regeneration from such callus tissues.

The *Zoysia japonica* Steud., also known as Korean grass, is a species of the warm season turfgrass and widely distributed in the Far-Eastern Asia, including Korea and Japan, and in the temperate zone. Its use is rapidly expanding in USA and other countries in recent years due to its extraordinary characteristics, such as resistance to drought and cold stress and capacity to rapidly recover from traffic damage. It also grows well in poor soil in virtually all climates. Due to these traits, it is widely used for golf courses, athletic fields, roadsides, home gardens, and riverbanks. As its market size is rapidly growing, new varieties with improved resistance to pathogens, herbicides, and environmental stress are demanded by customers. Classical breeding methods have been used to develop such traits, but many laboratories and institutes are striving to find molecular biological methods to genetically engineer the turfgrass. One essential prerequisite for this genetic manipulation is an efficient plant tissue culture and regeneration system. Seed-derived calli and immature embryonic cells have been evaluated for this purpose, and various combinations of media and plant growth hormones have been tested. However, the reported conditions for callus induction and growth and plant regeneration varies among different turfgrass species, and even the calli from a specific species exhibit a broad range of diversity in terms of callus morphology and structural organization, depending on the callus induction conditions.

With rapid accumulation of technological information on the plant tissue culture and genetic transformation in plants, a gene of interest can now be routinely introduced into any desired plants to enhance commercial value, yield, and environmental adaptability. In the present invention, we provide the optimised conditions for callus induction and growth, the morphological clues for isolation of functionally homogeneous callus, and the efficient system for plant regeneration of the zoysiagrass.

As used herein, the term "callus" refers to a group of undifferentiated cells derived from any plant parts of higher plants, preferentially those from mature seeds of the zoysiagrass. The term "plant regeneration" refers to the generation of fully differentiated plants from undifferentiated plant tissues, especially callus.

SUMMARY OF THE INVENTION

The present invention relates to an experimental method to efficiently induce and grow calli from mature seeds of the zoysiagrass that can be readily used for the genetic transformation. Such an experimental method may be applied to any turfgrass species, but more preferentially to the zoysiagrass.

The present invention also relates to the media compositions and optimal combinations of different plant growth hormones for efficient callus induction and growth. Callus induction rate was the highest when the seeds were cultured on the Murashige & Skoog (MS) medium containing 1.5–2.5 mg/L 2,4-dichlorophenoxyacetic acid, 0.15–0.25 mg/L 6-benzylaminopurine, 3.5–4.5 mg/L thiamine-HCl, and 80–120 mg/L ($\alpha$-ketoglutaric acid. On the contrary, callus growth was most efficient when calli was cultured on the MS medium containing 0.4–0.6 mg/L 2,4-dichlorophenoxyacetic acid, 0.015–0.025 mg/L 6-benzylaminopurine, 3.5–4.5 mg/L thiamine-HCl, and 80–120 mg/L $\alpha$-ketoglutaric acid.

Also, provided in the invention includes an efficient plant regeneration system. The regeneration rate was the highest when calli were transferred onto the MS medium supplemented with 2.5–3.5% maltose as a sugar source and 0.8–1.2 mg/L 6-benzylaminopurine or 0.8–1.2 mg/L thidiazuron (TDZ).

The present invention relates to the critical factors that influence the callus induction efficiency and the morphological types of calli that exhibit a high potential for shoot regeneration and a minimized frequency of albino plants. The relative ratio of 2,4-dichlorophenoxyacetic acid and 6-benzylaminopurine greatly influenced the callus types. Four morphologically distinct callus types (types I–IV) were induced by different concentration ratios of 2,4-dichlorophenoxyacetic acid and 6-benzylaminopurine. Types I–III calli readily produced shoots upon subculture. However, the watery type IV calli produced roots but not shoots. Among the types I–III calli, the type I calli exhibited the highest frequency (82%) of shoot regeneration and the lowest frequency (4%) of albinism.

Therefore, the present invention provides the media compositions and combination ratios of different growth hormones optimized for efficient induction of calli that are readily regenerated to shoots; the morphological clues that can be used to select potential calli for plant regeneration; the media components, such as sugars and cytokinins, for optimal callus induction and growth.

A; Type I callus with yellow, differentiated structure induced on the MS medium containing 1 mg/L 2,4-dichlorophenoxyacetic acid and 0.2 mg/L 6-benzylaminopurine.

B; Type II callus with white color and non-friable, compact structure induced on the MS medium containing 2 mg/L 2,4-dichlorophenoxyacetic acid and 0.2 mg/L 6-benzylaminopurine.

C; Type III callus with yellow color and friable, compact structure induced on the MS medium containing 4 mg/L 2,4-dichlorophenoxyacetic acid and 0.2 mg/L 6-benzylaminopurine.

D; Type IV callus with light yellow color and friable, soft, and watery appearance induced on the MS medium containing 1 mg/L 2,4-dichlorophenoxyacetic acid and 0.2 mg/L 6-benzylaminopurine.

Figure 2:
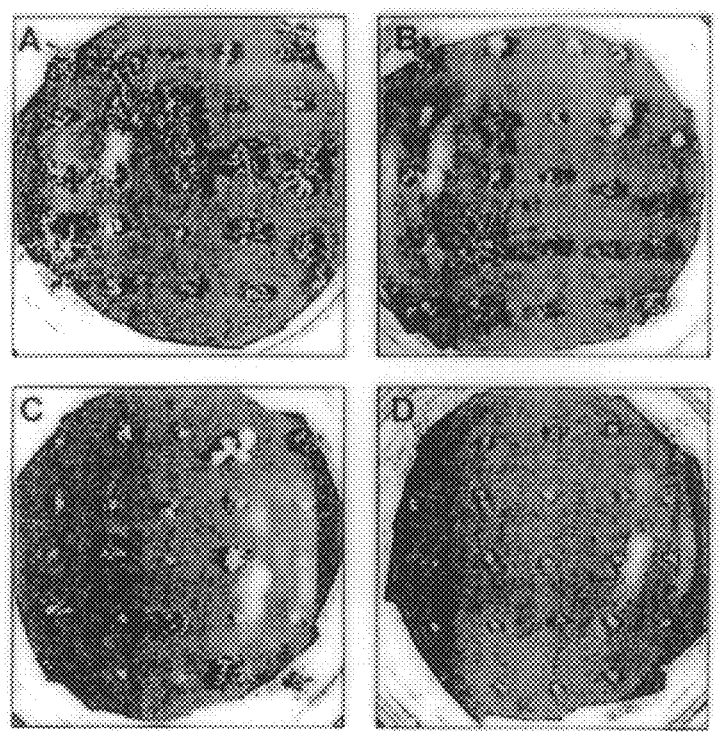

FIG. 2 shows the shoot regeneration of each callus type. Calli were transferred onto the MS medium containing 1 mg/L 6-benzylaminopurine and 30 g/L maltose and grown for 2 weeks in the light.

A; Shoots from callus type I. B; Shoots from callus type II. C; Shoots from callus type III. D; Shoots from callus type IV.

Figure 3:
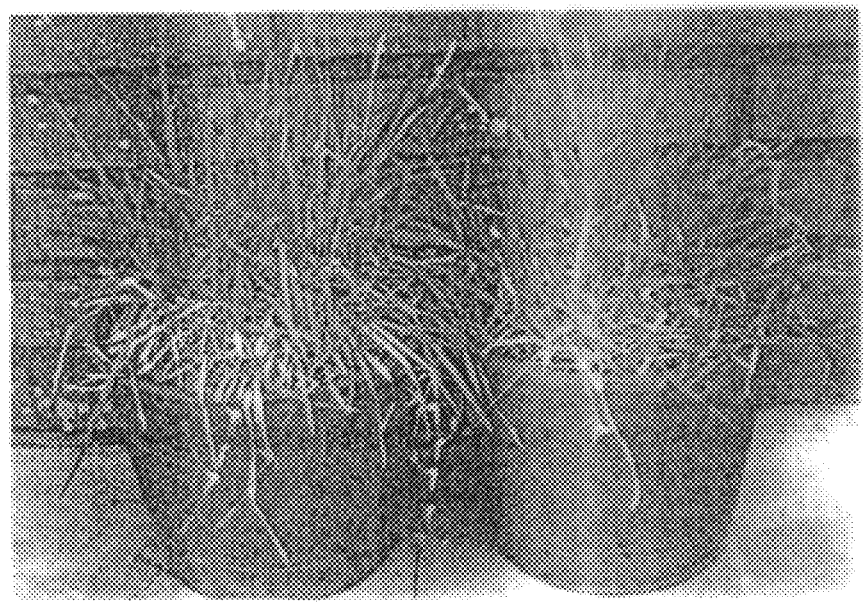

FIG. 3 shows mature zoysiagrass plants established in soil and grown for 3 months after regeneration from mature seed-derived callus. Two independent plants are displayed.

DETAILED DESCRIPTION OF THE INVENTION

This invention relates to the tissue culture conditions optimized for efficient callus growth and plant regeneration of zoysiagrass (*Zoysia japonica* Steud.) and to the morphological characteristics of calli that can be readily regenerated to mature plants. The present invention also provides the methods and processes for finding out optimised conditions for tissue culture of any higher plants that are reluctant to genetic transformation.

Genetic transformation is a powerful way to develop new varieties of a plant species with new agronomically important traits, such as improved growth rate, enhanced resistance to biotic and abiotic stress, increased yield, and flexible adaptability to environmental stress. The prerequisites for this plant genetic engineering are an efficient system for tissue culture and plant regeneration and a feasible gene delivery device. The latter has been well advanced genetically and technologically, and a gene of interest can be delivered to any plant species of interest. However not all plant species are readily accessible to genetic transformation. Some agronomic plants, especially monocots, are known to be reluctant to genetic manipulation. Turfgrass is widely used for multiple purposes, including golf courses, lawn grounds, home gardens, and recreation parks and is emerging as a potential commercial target for plant biotechnological applications in recent years. However, experimental information on the efficient and reliable system for turfgrass tissue culture and plant regeneration is very limited.

Therefore the present invention provides the optimised conditions for callus induction and growth from mature seeds of the zoysiagrass. The zoysiagrass is a subtype of the warm season turfgrass and widely distributed in the temperate zone. Calli are most efficiently induced when seeds are germinated and grown on the MS media containing 2,4-dichlorophenoxyacetic acid, 6-benzylaminopurine, thiamine-HCl, and (α-ketoglutaric acid, at the concentrations of 2 mg/L, 0.2 mg/L, 4 mg/L, and 100 mg/L, respectively. The plant tissue culture and callus induction experiments can be routinely performed in any plant molecular laboratories and well known to the art.

The present invention also relates to the optimal media compositions suitable for efficient call induction from mature seeds of zoysiagrass. Calli are most highly induced on the MS media with a frequency of 5.8% among the 5 different basal media tested, including MS, R2 (2.8%), Linsmaier & Skoog medium (LS) (1.4%), N6 (0.7%), and Gamborg B5 medium (B5) (0.7%).

Also, the present invention provides ideal sugars and cytokinins and their optimal concentrations for efficient plant regeneration. Among the five sugars widely used for plant tissue culture, such as sucrose, glucose, maltose, galactose, and fructose, maltose and glucose are most efficient in plant regeneration. Particularly, shoots are at least 10 times more efficiently regenerated on the maltose-containing media than on the sucrose-containing media. In addition, shoots with a height of higher than 2 mm are regenerated with a frequency of 51% when 30 g/L maltose is used. However, higher than 6% maltose confers a physical stress on the cultured cells, as evidenced by the red color appeared at the margins of the leaves and stems of the regenerated shoots due to the accumulation of anthocyanin pigments.

Furthermore, the present invention provides the morphological clues that can be used to select the callus types that are efficiently regenerated to plants. Comparison of morphological features, colors, and rigidities of calli can be employed to discriminate four distinct callus types (I–IV). Callus types with compact and rigid appearance (types I–III) are efficiently regenerated to plants. However, the soft and watery calli (type IV) did not show any regeneration under all the culture conditions tested. The type I calli are induced most efficiently on the MS medium supplemented with 1 mg/L 2,4-dichlorophenoxyacetic acid and 0.2 mg/L 6-benzylaminopurine with a frequency of 16.3%. On the contrary, they are not induced at all when more than 2 mg/L 2,4-dichlorophenoxyacetic acid and 4 mg/L 6-benzylaminopurine are supplemented. Shoot induction is also most efficient from the type I calli with a frequency of 82%. In addition, the albino shoots are minimally induced from the type I calli. The term "shoot' in the invention refers to a differentiated tissue with green color derived from calli, that has a capacity to eventually grow to a mature plant.

The present invention therefore can be applied to tissue cultures of zoysiagrass and closely related turfgrass as well as possibly of plant species that belong to the Gramineae Family to get highly potent calli from mature seeds for genetic transformation. It is particularly possible to efficiently regenerate plants from calli transformed with plant expression vector constructs containing genes of agronomic interests. Technical procedures for the development of such genetically engineered plants are well known to the art.

EXAMPLES

Plant Materials and Growth Conditions

Seeds of zoysiagrass (*Zoysia japonica* Steud.), from which seed coats were first removed, were sterilized by soaking in 70% ethyl alcohol for 1 min and subsequently in 5% sodium hypochlorite solution supplemented with 0.001% (v/v) Tween 20 for 15 min. The sterilized seeds were then thoroughly rinsed with sterilized distilled water 3–4 times. They were then germinated and grown for 2 weeks on the N6 media (pH 5.8) containing 1 mg/L 2,4-dichlorophenoxyacetic acid, 3% sucrose, and 0.2% gelite and subject to callus induction. The callus induction and growth was carried out in a controlled environment culture room set at 26° C. and 70% humidity in the dark.

Screening of Media Compositions for Efficient Plant Regeneration

To precisely refine the optimal media compositions for the generation of calli from which plants are efficiently regenerated, the plant regeneration frequency of each callus type was measured on different basal media. The types I–III calli were dissected into spherical lumps with a diameter of 3 mm and placed and grown on different basal media supplemented with different components. The basal media tested include MS (Murashige and Skoog, 1962), N6, LS (Linsmaier and Skoog, 1965), B5 (Gamborg et al., 1968), and R2 (Ohira et al., 1973). They were supplemented with various growth regulatory materials, such as 2,4-dichlorophenoxyacetic acid, 6-benzylaminopurine, thiamine-HCl, or α-ketoglutaric acid, whenever required. For each medium, 50 culture tubes (9 cm×1.5 cm), each containing 3 callus lumps, were included. All callus cultures were maintained under the identical condition. After a two-month growth, the total number of the regenerated plants from each treatment was counted.

Effects of Plant Growth Hormones on Callus Induction Efficiency

To examine the effects of plant growth hormones on the callus induction efficiency and the callus morphology, sterilized seeds were placed and cultured on the MS plates supplemented with 4 mg/L thiamine-HCl and 100 mg/L α-ketoglutaric acid. The MS plates, each with a diameter of 9 cm, were further supplemented with various amounts of 2,4-dichlorophenoxyacetic acid (0, 1, 2, 4, 8 mg/L) and 6-benzylaminopurine (0, 0.02, 0.2, 2, 4 mg/L). One hundred seeds were grown per each MS plate, and 3 plates were used for each treatment group. After three months, the number of seeds from which calli had been induced was counted. For the morphological classification of calli, calli were induced and grown on the MS media supplemented with 6-benzylaminopurine and 2,4-dichlorophenoxyacetic acid under the identical condition as described above for three months. They could be morphologically classified into four distinct groups (I–IV), based on the callus morphology, color, and rigidity.

Table 1. lists the morphological characteristics of each callus type induced from mature seeds of zoysiagrass cultured on the MS media containing 0 to 8 mg/L 2,4-dichlorophenoxyacetic acid and 0 to 4 mg/L 6-benzylaminopurine for 3 months.

TABLE 1

| Callus types | Color | Morphology/structure |
| --- | --- | --- |
| Type I | Yellow | Differentiated structure |
| Type II | White | Non-friable and compact |
| Type III | Yellow | Friable and compact |
| Type IV | Light yellow | Friable, soft, and watery |

Effects of Sugars and Cytokinins on Plant Regeneration

To examine the effects of various sugars on the plant regeneration efficiency from calli, the type I calli were dissected into lumps with a diameter of 2 mm and grown on the MS media containing 1 mg/L TDZ and 3% (w/v) fructose, galactose, glucose, maltose, or sucrose. For each treatment, 3 MS plates, each with 25 calli, were used. The regeneration frequency was displayed as the number of calli from which plants were regenerated to a shoot with a height of at least 2 mm after 2 weeks. Maltose was the most efficient for plant regeneration among the sugars tested. To determine the optimal concentration of maltose, the type I calli were grown on the MS media supplemented with various concentrations of maltose at 1.5, 3.0, 4.5, 6.0, 7.5, or 9%. The regeneration frequency was also displayed as described above.

To investigate the effects of various cytokinins, the type I calli were grown on the MS media supplemented with 3% maltose and 0.2% gelite. The media were additionally supplemented with 1 or 4 mg/L of kinetin, 6-benzylaminopurine, or TDZ. Each treatment consisted of 3 MS plates, each with 16 calli. The regeneration frequency was displayed as the number of green shoot after growth under the light condition (30 $\mu mol.m^{-2}.s^{-1}$).

Plant Regeneration Efficiency of Each Callus Type

The four distinct calli types induced in the dark were dissected into lumps, each with a fresh weight of 10 mg, and grown on the MS media supplemented with 1 mg/L 6-benzylaminopurine and 3% maltose. Twenty-five callus lumps were placed per each MS plate. The number of the regenerated plants with a height of at least 5 mm was counted after 2 weeks. The regeneration rate was displayed as a percentage of the total number of callus lumps. The callus growth was maintained under the light condition (30 $\mu mol.m^{-2}.s^{-1}$).

Results

Effects of Media Compositions on Callus Induction

To investigate the effects of different media compositions on the callus induction efficiency, the calli induced from mature seeds were grown on 5 different basal media with different compositions for 2 months, and the number of calli that are capable of regenerating plants was counted.

Table 2 shows the effects of different media on the regenerative callus (RC) induction from mature seeds of zoysiagrass. Two-week old calli on the N6 medium were plated and grown on the different basal media containing 1 mg/L 2,4-dichlorophenoxyacetic acid, 0.1 mg/L 6-benzylaminopurine, 4 mg/L thiamine-HCl and 100 mg/L α-ketoglutaric acid for 2 months.

TABLE 2

| Media | Number of calli tested | Number of RC (%) |
|---|---|---|
| MS | 139 | 8 (5.8) |
| LS | 141 | 2 (1.4) |
| N6 | 144 | 1 (0.7) |
| B5 | 141 | 1 (0.7) |
| R2 | 141 | 4 (2.8) |

As illustrated in Table 2, the callus induction rate was 5.8% on the MS medium, which is much higher than those on the R2 (2.8%), LS (1.4%), N6 (0.7%), and B5 (0.7%) media. This pattern is similar to those in the previous results (Inokuma et al., 1996). It has been suggested that the MS medium is most suitable for callus induction from turfgrass seeds. It is interesting that the zoysiagrass calli were induced most efficiently on the MS medium that contains relatively high concentrations of salts compared to other basal media. On the contrary, corn and rice plants that also belong to the Gramineae Family, exhibited relatively lower efficiency on the MS media (Hiel et al., 1994; Carvalho et al., 1997).

Effects of Plant Growth Hormones on Callus Induction Efficiency

To investigate the effects of plant growth hormones on the callus induction, the mature seed-derived callus induction rates were measured on the MS media supplemented with different amounts of 2,4-dichlorophenoxyacetic acid and 6-benzylaminopurine after grown for three months. The most efficient callus induction was observed from the MS media with 1 mg/L 2,4-dichlorophenoxyacetic acid and 0.2 mg/L 6-benzylaminopurine at the rate of 18.3% (Table 3).

Table 3 shows the effects of different concentration combinations of 2,4-dichlorophenoxyacetic acid and 6-benzylaminopurine on the regenerative callus (RC) induction from mature seeds of zoysiagrass. Seeds were plated and grown on the MS media containing 4 mg/L thiamine-HCl, 100 mg/L α-ketoglutaric acid, and different concentration combinations of 2,4-dichlorophenoxyacetic acid and 6-benzylaminopurine for 3 months.

TABLE 3

| 2,4-dichlorophenoxyacetic acid (mg/L) | 6-benzylaminopurine (mg/L) | Number of seeds tested | Number of callus producing seeds (%) |
|---|---|---|---|
| 0 | 0 | 337 | 0 (0) |
| 0 | 0.02 | 250 | 0 (0) |
| 0 | 0.2 | 233 | 0 (0) |
| 0 | 2 | 239 | 0 (0) |
| 0 | 4 | 337 | 0 (0) |
| 1 | 0 | 304 | 47 (15.5) |
| 1 | 0.02 | 421 | 65 (15.4) |
| 1 | 0.2 | 389 | 49 (12.6) |
| 1 | 2 | 360 | 61 (16.9) |
| 1 | 4 | 363 | 39 (15.5) |
| 2 | 0 | 115 | 18 (10.7) |
| 2 | 0.02 | 334 | 54 (16.2) |
| 2 | 0.2 | 355 | 65 (18.3) |
| 2 | 2 | 348 | 59 (17.0) |
| 2 | 4 | 250 | 39 (15.6) |
| 4 | 0 | 121 | 19 (15.7) |
| 4 | 0.02 | 330 | 46 (13.9) |
| 4 | 0.2 | 344 | 56 (16.3) |
| 4 | 2 | 314 | 35 (11.1) |
| 4 | 4 | 336 | 20 (6.0) |
| 8 | 0 | 341 | 38 (11.1) |
| 8 | 0.02 | 354 | 35 (9.9) |

TABLE 3-continued

| 2,4-dichlorophenoxyacetic acid (mg/L) | 6-benzylaminopurine (mg/L) | Number of seeds tested | Number of callus producing seeds (%) |
|---|---|---|---|
| 8 | 0.2 | 362 | 28 (7.7) |
| 8 | 2 | 296 | 19 (6.4) |
| 8 | 4 | 339 | 14 (4.1) |

However, no calli were induced from the MS medium without 2,4-dichlorophenoxyacetic acid. Some calli were induced, although not very efficient, on the MS media supplemented with higher than 4 mg/L 2,4-dichlorophenoxyacetic acid or 6-benzylaminopurine, but the calli became brownish as they grew and eventually died. These results indicate that the concentrations of 2,4-dichlorophenoxyacetic acid and 6-benzylaminopurine are critical for the efficient callus induction from mature seeds, as has been reported with other turfgrass and corn plant (Carvalho et al., 1997).

Figure 1:
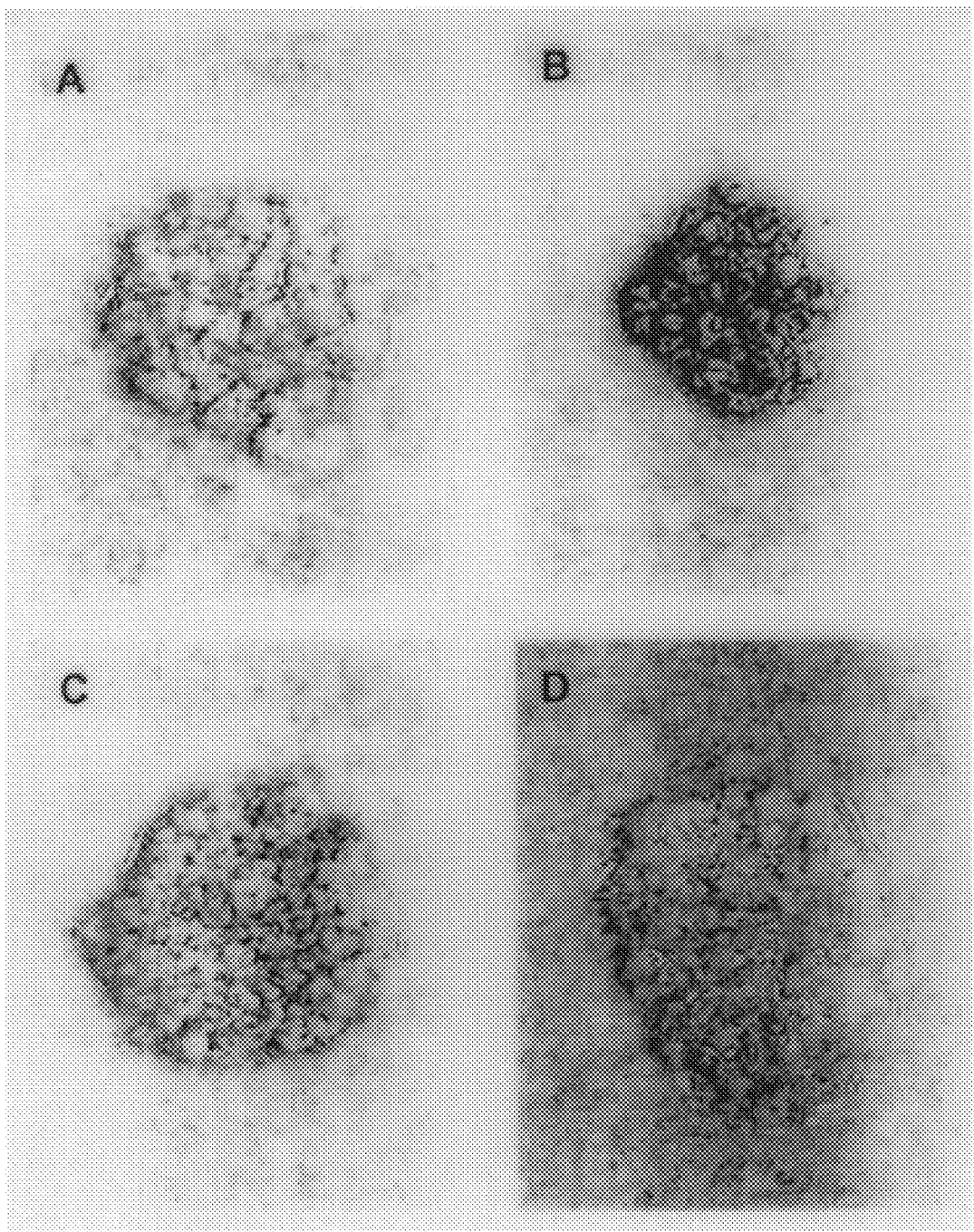
FIG. 1 shows the four morphologically distinct types of calli induced from mature seeds of zoysiagrass (*Zoysia japonica* Steud.) grown on the MS media containing various combinations of 2,4-dichlorophenoxyacetic acid and 6-benzylaminopurine for 5 weeks in the dark.

Generation of Distinct Callus Types by Different Concentrations of Growth Hormones Calli induced on the MS media supplemented with different concentration combinations of 2,4-dichlorophenoxyacetic acid and 6-benzylaminopurine were morphologically and physiologically analysed. Four distinct callus types (types I to IV) could be apparently discriminated by callus color, morphology, and rigidity (FIG. 1). The type I calli were yellowish and exhibited a somewhat differentiated structure. The type II calli were white and had a rigid structure. The type III calli were slightly yellowish and had a compact, rigid, but fragile structure. The type IV calli had a watery, soft appearance.

The type I calli were induced with the highest frequency of 16.3% among the four callus types on the MS plates with 1 mg/L 2,4-dichlorophenoxyacetic acid and 0.2 mg/L 6-benzylaminopurine but were not induced at all on the MS plates with higher than 2 mg/L 2,4-dichlorophenoxyacetic acid and 4 mg/L 6-benzylaminopurine. The induction of the type II calli were the least efficient among the four callus types. They were induced only on the MS plates with 2 mg/L 2,4-dichlorophenoxyacetic acid and 0.2 mg/L 6-benzylaminopurine with a frequency of 1.5%. The type III calli were efficiently induced at most of the growth hormone concentrations tested with the highest frequency of 14.3% on the MS plates with 2 mg/L 2,4-dichlorophenoxyacetic acid and 0.2 mg/L 6-benzylaminopurine. The type IV calli were very efficiently induced on all growth hormone concentrations tested with a frequency range of 83.1-100%.

Table 4 shows the effects of different concentration combinations of 2,4-dichlorophenoxyacetic acid and 6-benzylaminopurine on the morphology of callus derived from mature seeds of zoysiagrass. Seeds were plated on the MS media containing 4 mg/L thiamine-HCl, 100 mg/L α-ketoglutaric acid, and different concentration combinations of 2,4-dichlorophenoxyacetic acid and 6-benzylaminopurine for 3 months. Callus morphologies were rated by; type I: with yellow and differentiated structure, type II: with white, non-friable, and compact structure, type III: with yellow, friable, and compact structure, Type IV: with whitish yellow, friable, soft, and watery appearance. Type I~III represents the sum of the numbers of types I to III.

TABLE 4

Number of calli showing various morphologies (%)

| 2,4-dichlor ophenoxyace tic acid (mg/L) | 6-benzyl amino purine (mg/L) | Number of calli tested | Type I | Type II | Type III | Type I–III | Type IV |
|---|---|---|---|---|---|---|---|
| 1 | 0    | 47 | 2 (4.3)  | 0 (0)   | 2 (4.3)  | 4 (8.5)   | 43 (91.5) |
| 1 | 0.02 | 65 | 6 (9.2)  | 0 (0)   | 0 (0)    | 6 (9.2)   | 59 (90.8) |
| 1 | 0.2  | 49 | 8 (16.3) | 0 (0)   | 0 (0)    | 8 (16.3)  | 41 (83.7) |
| 1 | 2    | 61 | 6 (9.8)  | 0 (0)   | 1 (1.6)  | 7 (11.5)  | 54 (88.5) |
| 1 | 4    | 39 | 4 (10.3) | 0 (0)   | 0 (0)    | 4 (10.3)  | 35 (89.7) |
| 2 | 0    | 18 | 0 (0)    | 0 (0)   | 1 (5.6)  | 1 (5.6)   | 17 (94.4) |
| 2 | 0.02 | 54 | 2 (3.7)  | 0 (0)   | 1 (1.9)  | 3 (5.6)   | 51 (94.4) |
| 2 | 0.2  | 65 | 8 (12.3) | 1 (1.5) | 2 (1.5)  | 11 (16.9) | 54 (83.1) |
| 2 | 2    | 59 | 5 (8.5)  | 0 (0)   | 4 (6.8)  | 9 (15.3)  | 52 (84.7) |
| 2 | 4    | 39 | 0 (0)    | 0 (0)   | 0 (0)    | 0 (0)     | 39 (100)  |
| 4 | 0    | 19 | 0 (0)    | 0 (0)   | 1 (5.3)  | 1 (5.3)   | 18 (94.7) |
| 4 | 0.02 | 46 | 0 (0)    | 0 (0)   | 1 (2.2)  | 1 (2.2)   | 44 (95.7) |
| 4 | 0.2  | 56 | 0 (0)    | 0 (0)   | 8 (14.3) | 8 (14.3)  | 48 (85.7) |
| 4 | 2    | 35 | 0 (0)    | 0 (0)   | 1 (2.9)  | 1 (2.9)   | 34 (97.1) |
| 4 | 4    | 20 | 0 (0)    | 0 (0)   | 0 (0)    | 0 (0)     | 20 (100)  |
| 8 | 0    | 38 | 0 (0)    | 0 (0)   | 0 (0)    | 0 (0)     | 38 (100)  |
| 8 | 0.02 | 35 | 0 (0)    | 0 (0)   | 1 (2.9)  | 1 (2.9)   | 34 (97.1) |
| 8 | 0.2  | 28 | 0 (0)    | 0 (0)   | 1 (3.6)  | 1 (3.6)   | 10 (96.4) |
| 8 | 2    | 19 | 0 (0)    | 0 (0)   | 2 (10.5) | 2 (10.5)  | 17 (89.5) |
| 8 | 4    | 14 | 0 (0)    | 0 (0)   | 0 (0)    | 0 (0)     | 14 (100)  |

Interestingly, the four callus types exhibited highly variable capacities for plant regeneration. Plants were regenerated from the types I–III, although the efficiencies were variable among the callus types. However, the type IV calli did not show any capacity for plant regeneration under all growth conditions tested (FIG. 2). Of particular interest is the fact that when any of the callus types I–III were subject to subcultures, all four types of calli were induced but with some variations among the callus types. On the contrary, only the type IV calli were observed from the subculture of the type IV calli. These indicate that callus types are greatly influenced by growth hormones and their concentrations used, which is similar to the previous observations on Kentucky bluegrass and corn plant (Ke and Lee, 1996; Carvalho et al., 1997). Furthermore these results suggest that when calli induced from seeds or other plant tissues are used for plant regeneration, each callus type should be carefully evaluated for their regeneration capacities.

Effects of Different Sugars on Plant Regeneration

The effects of different sugars on the plant regeneration efficiency from calli were examined using the shoot induction media (SIM) supplemented with different sugars. The plant regeneration efficiency was the highest on the SIM with sucrose among the 5 different sugars tested. However, the number of plants regenerated per callus lump was much higher on the SIM with either maltose or glucose. Particularly, the plants with a height of bigger than 2 mm was 10 times more efficiently regenerated on the SIM with maltose than on the SIM with sucrose (Table 5). On the contrary, no plants were regenerated from the SIM with galactose, and the calli became brownish and eventually died.

Table 5 shows the effects of sugars on the shoot regeneration from calli derived from mature seeds of zoysiagrass. Type I calli were cultured on the MS medium containing 1 mg/L TDZ for 2 weeks. Each value in the second column represents a mean calculated from 25 calli per each experiment. Each value in the third column represents a mean calculated from 10 calli for each experiment.

TABLE 5

| Sugars (30 g/L) | Calli with green shoot (%) | Number of shoots per callus lump | Shoots over 2 mm (%) |
|---|---|---|---|
| Glucose   | 37.3 ± 2.7 | 6.9 ± 0.3c | 39.8 ± 7.3 |
| Maltose   | 33.3 ± 2.7 | 9.4 ± 0.3  | 46.4 ± 5.0 |
| Sucrose   | 45.3 ± 9.3 | 4.5 ± 0.1  | 4.5 ± 0.2  |
| Fructose  | 17.3 ± 2.7 | 4.4 ± 0.8  | 12.6 ± 3.0 |
| Galactose | 0          | 0          | 0          |

The effect of maltose was further investigated by titrating its concentration in the SIM. The number of calli that is capable of regenerating plants and the number of plants regenerated per callus lump were relatively high when lower than 3% of maltose was used. However, the regeneration frequency of plants with a height of bigger than 2 mm was the highest with a frequency of 5 1% when 3 0 g/L maltose was used.

Table 6 shows the effects of different concentrations of maltose on the shoot regeneration from mature seed-derived calli of zoysiagrass. Type I calli were cultured on the MS medium containing 1 mg/L TDZ and various concentrations of maltose for 2 weeks.

TABLE 6

| Maltose (g/L) | Calli with green shoot (%) | Number of shoots per callus lump | Shoots over 2 mm (%) |
|---|---|---|---|
| 15 | 37.3 | 9.9 ± 0.1  | 45.2 ± 3.4 |
| 30 | 36.0 | 12.9 ± 1.2 | 51.4 ± 3.9 |
| 45 | 32.0 | 10.2 ± 1.3 | 32.1 ± 3.6 |
| 60 | 29.3 | 4.9 ± 0.6  | 14.5 ± 5.5 |
| 75 | 30.7 | 8.3 ± 0.9  | 27.3 ± 4.0 |
| 90 | 28.0 | 2.5 ± 0.3  | 6.7 ± 0.2  |

The superior effect of maltose compared to that of the generally used sucrose on the plant regeneration from zoysiagrass calli is similar to those observed on rice, wheat, and creeping bentgast and Brettell, 1990; Asano et al., 1994). When maltose was used at a higher concentration, such as 6.0%, the margins of the leaves and stems in the regenerated plants exhibited color caused by accumulation of anthocyanin-related pigments. This may be related with that observed on strawberry culture cells grown in the presence of high sugar concentration, possibly because the concentrated sugar confers a physical stress on the culture cell (Sato et al., 1996).

Effect of Cytokinins on Plant Regeneration from Calli

Different cytokinins at various concentrations also influenced the plant regeneration efficiency of calli. The number of callus lumps that are capable of regenerating plants, the number of plants regenerated per callus lump, and the height of each plant (higher than 5 mm) were the highest when 1 mg/L of 6-benzylaminopurine and TDZ were included.

Table 7 shows the effects of various cytokinins on the shoot induction from callus derived from mature seeds of zoysiagrass. Type I calli were cultured on the MS medium containing 30 g/L maltose and different cytokinins for 2 weeks.

TABLE 7

| Growth regulators | (mg/L) | Number of calli tested | Number of calli with shoots | Number of shoots per callus lump | Number of shoots over 5 mm |
|---|---|---|---|---|---|
| Control | 0 | 44 | 6 | 4.0 | 0 |
| Kinetin | 1 | 44 | 8 | 3.0 | 0 |
|  | 4 | 44 | 7 | 1.7 | 0 |
| 6-benzylaminopurine | 1 | 44 | 17 | 5.2 | 19 |
|  | 4 | 44 | 9 | 3.7 | 1 |
| TDZ | 1 | 44 | 17 | 4.8 | 14 |
|  | 4 | 44 | 10 | 4.1 | 1 |

When only the TDZ was included, plant regeneration was observed, but the plants did not continue growing. These indicate that both the 6-benzylaminopurine and TDZ are required for optimal plant regeneration. Although TDZ is necessary for plant regeneration, high concentration of TDZ exhibited some harmful effects. In the presence of high concentration of TDZ, plants with abnormal morphology were observed at a high frequency, and the plant growth was also severely retarded, as observed with the peanut plant cell culture (Akasaka et al., 2000). An ideal way to use TDZ is that it should be included in the medium for the plant regeneration but removed later from the media for the optimal growth of plants.

Plant Regeneration Efficiency of Each Callus Type

To more systematically access to the potency of each callus types in plant regeneration, each callus type was separately subject to plant regeneration analysis. No plant regeneration was observed from the type IV calli, and the calli gradually became brownish after 10 days (FIG. 2). Other callus types (I to IV) were highly capable of regenerating plants. Especially the type I calli exhibited the highest regeneration frequency of 82% and a minimal frequency of albino plants.

Table 8 shows the capacity of each callus type for the shoot regeneration. Twenty-five calli per each callus type were cultured on the MS medium containing 1 mg/L 6-benzylaminopurine and 30 g/L maltose for 2 weeks.

TABLE 8

| Callus types | Calli with green shoots (%) | Calli with albino shoots (%) |
|---|---|---|
| Type I | 82 | 4 |
| Type II | 62 | 26 |
| Type III | 38 | 22 |
| Type IV | 0 | 0 |

When the regenerated plants were transferred to the MS media without any growth hormones for root induction and subsequently transferred to soil, they grew normally to fully differentiated, adult plants (FIG. 3).

Notably, the plant regeneration capacity of the types I to III calli did not decrease even after a long period of subculture (one year or longer). It has been reported that the calli of the grasses gradually lose their potency of plant regeneration through repeated subcultures, and more albino plants occurred. The occurrence of albino plants is a critical barrier to successful plant tissue cultures, and many efforts were put to suppress their occurrence by modifying media compositions, growth hormones, and inorganic salts (Cho et al., 1998). In this invention, we were able to develop a system to efficiently suppress the occurrence of albino plants.

The present invention provides optimal media compositions and culture conditions for callus induction from mature seeds of zoysiagrass that are capable of efficiently regenerating plants but with a minimal frequency of albino plants. This culture system could provide an invaluable tool for genetic transformation of zoysiagrass, especially when a gene of interest is to be introduced into zoysiagrass with an aim to improve resistance to biotic and abiotic stress and to modulate the growth rate. The present invention could be also applied to other turfgrass species for such purposes.

REFERENCES

Akasaka, Y., Daimon, H., Mii, M. (2000). Improved plant regeneration from cultured leaf segments in peanut (Arachis hypogaea L.) by limited exposure to thidiazuron. Plant Sci. 156: 169–175.

Asano, Y., Ito, Y., Ohara, M., Sugiura, K., Fujiie, A. (1994). Improved regeneration response of creeping bentgrass and japonica rice by maltose and lactose. Plant Cell Tiss. Org. Cult. 39: 101-103.

Carvalho, C. H. S., Bohorova, N., Bordallo, P. N., Abreu, L. L., Valicente, F. H., Bressan W, Paiva, E. (1997). Type II callus production and plant regeneration in tropical maize genotypes. Plant Cell Rep. 17: 73–76.

Cho, M.-J., Jiang, W., Lemaux, P. G. (1998). Transformation of recalcitrant barley cultivars through improvement of regenerability and decreased albinism. Plant Sci. 138: 229–244.

Gamborg, O. L., Miller, R. A., Ojima, K. (1968). Nutrient requirements of suspension cultures of soybean root cells. Exp. Cell Res. 50: 151–158.

Hiei, Y., Ohta, S., Komari, T., Kumashiro, T. (1994). Efficient transformation of rice (Oryza sativa L.) mediated by Agrobacterium and sequence analysis of the boundaries of the T-DNA. Plant J. 6: 271–282.

Inokuma, C., Sugiura, K., Cho, C., Okawara, R., Kaneko, S. (1996). Plant regeneration from protoplasts of Japanese lawngrass. Plant Cell Rep. 15: 737–741.

Ke, S., Lee, C. W. (1996). Plant Regeneration in Kentucky bluegrass (Poa pratensis L.) Plant Cell Rep. 15: 882–887.

Last, D. I., Brettell, R. I. S. (1990). Embryo yield in wheat anther culture is influenced by the choice of sugar in the culture medium. Plant Cell Rep. 9: 14–16.

Linsmaier, E. M., Skoog, F. (1965). Organic growth factor requirements of tobacco tissue cultures. Physiol. Plant 18: 100–127.

Murashige, T., Skoog, F. (1962). A revised medium for rapid growth and bioassays with tobacco tissue cultures. Physiol. Plant 15: 473–497.

Ohira, K., Ojima, K., Fujiwara, A. (1973). Studies on the nutrition of rice culture. I. A simple, defined medium for rapid growth in suspension culture. Plant Cell Physiol. 14: 1113–1121.

Sato, K., Nakayama, M., Shigeta, J. (1996). Culturing conditions affecting the production of anthocyanin in suspended cell cultures of strawberry. Plant Sci. 113: 91–98.

What is claimed is:

1. A method for producing a zoysiagrass (Zoysia genus) comprising the steps of:

i) isolating zoysiagrass callus cells cultured from mature seeds in a callus induction medium comprising 1.5–2.5 mg/L of 2,4-dichlorophenoxyacetic acid, 0.15–0.25 mg/L of 6-benzylaminopurine, 3.5–4.5 mg/L of thiamine-HCl, and 80–120 mg/L of α-ketoglutaric acid, and ii) generating zoysiagrass from said cultured callus cells in a growth medium comprising 0.4–0.6 mg/L of 2,4-dichlorophenoxyacetic acid, 0.015–0.025 mg/L of 6-benzylaminopurine, 3.5–4.5 mg/L of thiamine-HCl, and 80–120 mg/L of α-ketoglutaric acid.

2. The method according to claim 1, wherein said zoysiagrass is any one of the turfgrass species.

3. The method according to claim 1, wherein the regeneration of the type I callus cells was isolated in an induction medium comprising 0.8–1.2 mg/L of 2,4-dichlorophenoxyacetic acid, 0.15–0.25 mg/L of 6-benzylaminopurine, 3.5–4.5 mg/L of thiamine-HCl, and 80–120 mg/L of α-ketoglutaric acid.

4. The method according to claim 1, wherein the growth medium further comprises 2.5–3.5 (w/v) % of maltose and 0.8–1.2 mg/L of 6-benzylaminopurine.

5. The method according to claim 1, wherein the growth medium further comprises 2.5–3.5 (w/v) % of maltose and 0.8–1.2 mg/L of thidiazuron(TDZ).

* * * * *